United States Patent [19]

Sugiyama et al.

[11] Patent Number: 5,906,937
[45] Date of Patent: *May 25, 1999

[54] CULTURE SKIN AND PROCESS FOR PREPARING THE SAME

[75] Inventors: Akihisa Sugiyama; Takeshi Moriyama; Kyoko Hamano, all of Kasugai, Japan

[73] Assignee: Menicon Co., Ltd., Nagoya, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/611,006

[22] Filed: Mar. 5, 1996

[30] Foreign Application Priority Data

Mar. 7, 1995 [JP] Japan .................................. 7-047587

[51] Int. Cl.$^6$ ..................................................... C12N 5/08
[52] U.S. Cl. ........................... 435/371; 435/347; 435/366
[58] Field of Search .................................... 435/347, 366, 435/371

[56] References Cited

U.S. PATENT DOCUMENTS 4,883,487  11/1989  Yoshizato et al. ........................ 623/15

FOREIGN PATENT DOCUMENTS 0 462 426  12/1991  European Pat. Off. .
4-332561  11/1992  Japan .
5-192363   8/1993  Japan .
7-59812    3/1995  Japan .

OTHER PUBLICATIONS

Doillon, et al., "Fibroblast and epidermal cell–type 1 collagen interactions: cell culture and human studies", Scanning Microscopy, vol. 2, No. 2, 985–992, Aug. 2, 1988.

*Primary Examiner*—Michael P. Woodward
*Assistant Examiner*—Brenda G. Brumback
*Attorney, Agent, or Firm*—Armstrong, Westerman, Hattori, McLeland & Naughton

[57] ABSTRACT

A process for preparing a culture skin which comprises the following steps:
  a) a step in which a culture skin matrix comprising a collagen sponge, a collagen sheet or a collagen gel is prepared in a means having a projection to provide said matrix with a penetrating pore,
  b) a step in which a skin-derived cell is seeded and cultured on said matrix, and
  c) a step in which the culture skin is provided with a penetrating pore by the means having the projection before said culture skin covers a skin defect, if necessary, the steps a) and b) are simultaneously carried out; a culture skin matrix and a culture skin obtained thereby. According to the present invention, a culture skin can be prepared wherein sufficient nutrition supply to epidermal cells and/or fibroblasts cultured and proliferated and discharge of exudate excessively pooled in the wound can be smoothly performed, while contraction is inhibited, by producing a penetrating pore in the culture skin before covering the wound with the culture skin with a means which requires no pretreatment in order to prevent the flow and loss of cells which are caused in seeding cells on a collagen matrix.

6 Claims, 4 Drawing Sheets

CULTURE SKIN AND PROCESS FOR PREPARING THE SAME

BACKGROUND OF THE INVENTION

The present invention relates to a culture skin and a process for preparing the same. More particularly, the present invention relates to a culture skin matrix, a culture skin and processes for preparing the same for reconstructing or healing a defect tissue in an early stage by applying the matrix or the skin to a skin defect such as a burn, a wound, a decubitus or a skin ulcer.

Hitherto a medical treatment used in general as therapy for a skin defect reaching to an upper layer of dermis such as a superficial dermal burn is a cover of the skin defect with wound dressings, ointment gauze or the like. However, when there is caused a skin defect reaching to a lower layer of dermis such as a deep dermal burn, a dermal burn or a decubitus in at least the second grade, self-reconstruction in a cutaneous tissue by proliferation of epidermal cells can not be expected. Therefore, such a defect has been treated by debriding a slough or an abnormal granulation tissue, reconstructing a normal granulation tissue by covering the defect with an allogenic skin, wound dressings or the like, and then reconstructing a skin by performing autologous split-thickness skin graft. In case of performing the autologous split-thickness skin graft, however, because a skin is taken from a normal position of a patient, there arises a problem as to restoration of appearance that the scar remain at the position. Further, in case that a wound extends in a wide range, it is difficult to carry out the autologous split-thickness skin graft.

In order to solve the problem, there have been developed a technique wherein epidermal cells or fibroblasts are taken from a small skin piece and mass-cultured in a culture flask, and various culture skins using these cultured cells.

The culture epidermis developed by Howard Green, James G. Rheinwald et al. is obtained by taking a skin of postage stamp size and mass-culturing cells derived from the skin in a culture flask to give an epidermal sheet. As to the sheet, the problem has been pointed out that taking ratio in autologous skin graft is low because basal cells being the most important cells are damaged by enzyme treatment in case of removing the sheet from the flask (see Yoshimitsu Kuroyanagi, Seitaizairyo (Biomaterial) Feb. 9, 1991).

Also, Eugene Bell et al. (see Science, 211, pages 1052–1054, 1981) developed a culture skin by mass-culturing each of epidermal cells and fibroblasts in a culture flask which were obtained by separating them from a skin, and stratifying epidermal cells on a collagen gel into which fibroblasts has been incorporated to give a culture skin. However, there was a fault that a collagen gel extremely contracts during cell culture.

Further, Steven Boyce et al. (see SURGERY, 103, pages 421–431, April, 1988) developed a culture skin by mass-culturing epidermal cells obtained from a skin and stratifying the epidermal cells on a matrix in a form of sponge which was obtained by adding a small amount of chondroitin-6-sulfate to collagen.

Also, culture skins having atelocollagen as a matrix are described in Japanese Unexamined Patent Publications No. 246371/1987 and No. 332561/1992. In Japanese Unexamined Patent Publication No. 246371/1987, a culture skin having an atelocollagen sheet as a matrix is described. In the above culture skin, however, there was a problem that taking ratio of epidermis is low in autologous skin graft. The reason is that the sheet has no penetrating pore, and nutrition being indispensable to cell proliferation and the like and being given from a covered wound face is hardly supplied through the sheet to epidermal cells on the opposite side of the sheet.

Also, in case of preparing a culture skin wherein only fibroblasts are taken into the skin, nutrition to be supplied from a covered wound face is hardly supplied throughout the culture skin. Therefore, proliferation and metabolism of fibroblasts are harmfully influenced and release of biologically active substances (e.g., growth factors, cytokines and the like) is not performed without hitch. These and the like often interfere with reconstruction of skin or good granulation.

There was the problem that a wound becomes a hotbed of infection by reason that exudate was excessively pooled in a wound and discharge of the exudate is not carried out properly, because of no penetrating pore.

In Japanese Unexamined Patent Publication No. 332561/1992, an atelocollagen sponge is described which is provided with a penetrating pore on purpose to solve the problem as described above. In case of providing the sponge with a penetrating pore, cells are flowed out through the pore and lost in being seeded. Therefore, pre-coating of the sponge with atelocollagen gel or the like before cell seeding is essential to the gel in order to compensate for such faults. There is the problem that such coating method is not only complicated but also expensive from the view points of cost for preparation of a culture skin. Therefore, development for more inexpensive and more simple alternative culture skin or preparation technique thereof has been desired.

The problems to be solved hitherto in a culture skin using collagen as a matrix were as follows:

1. contraction of a culture skin in cell culturing,
2. the problem that nutrition supply throughout cultured cells from a covered wound face is not smooth, because a culture skin matrix becomes a barrier after covering a defect tissue of a skin with a culture skin,
3. the problem that exudate is excessively pooled in a position where a defect tissue of a skin is covered with a culture skin after the covering, and
4. the problem that cells are flow out through a pore and are lost when being seeded, in the case a matrix is provided with a when penetrating pore in order to solve the above-mentioned points 2 and 3.

The present invention is made in order to solve the above points 1–4.

An object of the invention is to provide a culture skin for reconstructing or healing a defect tissue of a skin in an early stage by applying the culture skin to a skin defect such as a burn, a wound, a decubitus or a skin ulcer. More particularly, the object of the invention is to provide a culture skin which has a function by which there can be smoothly carried out nutrition supply from a covered wound face to cells of the culture skin and discharge of the exudate being excessively pooled in a wound, and is obtainable at a low cost without causing contraction.

A further object of the invention is to provide a culture skin matrix which can be used in the above-mentioned culture skin as a matrix.

A still further object of the invention is to provide processes for preparing the culture skin and the culture skin matrix.

These and other objects of the present invention will become apparent from the description hereinafter.

SUMMARY OF THE INVENTION

In accordance with the present invention, there is provided a process for preparing a culture skin which comprises the following steps:

a) a step in which a culture skin matrix comprising a collagen sponge, a collagen sheet or a collagen gel is prepared in a means having a projection to provide said matrix with a penetrating pore, b) a step in which a skin-derived cell is seeded and cultured on said matrix, and c) a step in which the culture skin is provided with a penetrating pore by the means having the projection before said culture skin is placed to cover a skin defect, if necessary, the steps a) and b) being simultaneously carried out. There is also provided a process for preparing a culture skin matrix comprising a collagen sponge, a collagen sheet or a collagen gel, in which said matrix is provided with a penetrating pore by a means having a projection before said matrix including a skin-derived cell is placed to cover a skin defect.

In the above-mentioned processes, preferably, the step b) is a step in which a skin-derived fibroblast is seeded and cultured on at least one side of said matrix, a step in which an epidermal cell is seeded and cultured on one side of said matrix, or a step in which a skin-derived fibroblast is seeded and cultured on at least one side of matrix and an epidermal cell is seeded and cultured on one side of said matrix; the step c) is accomplished by removing said projection from the matrix; the means having the projection is a support having a projection, a vessel having a projection, or a support or vessel having a projection with a removable sheet; the collagen is atelocollagen; and/or the culture skin matrix contains hyaluronic acid.

Further, according to the present invention, there are provided a culture skin matrix comprising a collagen sponge, a collagen sheet or a collagen gel, which has a hollow penetrating pore; and a culture skin which comprises a culture skin matrix comprising a collagen sponge, a collagen sheet or a collagen gel and having a hollow penetrating pore, and a skin-derived cell which is a fibroblast, an epidermal cell or a combination thereof.

In the above-mentioned culture skin matrix and culture skin, preferably, the culture skin matrix is provided with a hollow penetrating pore by a means having a projection; the culture skin matrix is set in the means having the projection and has a hollow penetrating pore produced by removing said projection from the matrix; the means having the projection is a support having a projection, a vessel having a projection, or a support or vessel having a projection with a removable sheet; the collagen is atelocollagen and/or the culture skin matrix contains hyaluronic acid, although the matrix and culture skin of the present invention can be provided with a penetrating pore by a means having a projection like a frog after the preparation of a culture skin matrix.

BRIEF EXPLANATION OF THE DRAWINGS

In FIG. 2, the symbol 1 represents a projection; the symbol 3 represents a vessel; and the symbol 4 represents a removable sheet.

In FIG. 3, the symbol 2 represents a pore (an opening), the symbol 4 represents a removable sheet.

In FIG. 4, the symbol 1 represents a projection; the symbol 4 represents a removable sheet; the symbol 5 represents a grip; and the symbol 6 represents a culture skin.

DETAILED DESCRIPTION

In the present specification, the term "hollow" means a state where no gel or the like is contained, for instance, a state where the above-mentioned projection is removed therefrom, and the like.

Examples of origin of the skin-derived cell used in the present invention are, for instance, a mammal such as human, and the like.

As the culture skin matrix of the present invention, there can be used collagen, gelatin, chitin, chitosan, polyglycolic acid, mucopolysaccharides such as chondroitin sulfate and hyaluronic acid, and the like. The above-mentioned collagen is preferably, for instance, one superior in biocompatibility such as atelocollagen.

The collagen sponge used in the present invention can be prepared by homogenizing a collagen solution, of which pH is adjusted to be acidic, with a homogenizer to give a homogenized solution into which bubbles are fully incorporated, pouring the obtained solution into a means having a projection, i.e., a vessel of plastic or the like in which a support having a projection is located, a vessel having a projection, or a support or vessel having a projection with a removable sheet, allowing the solution to stand under an atmosphere of ammonia gas to give a gel, lyophilizing the gel and introducing intermolecular-crosslinking into the gel with irradiation of ultraviolet rays (UV) or a crosslinking agent.

In the present invention, the collagen solution is obtained by preparing collagen from a bovine dermis or the like, adjusting the pH of a solution of the collagen to preferably 2–4 and preparing the collagen solution in a concentration of 0.2–3 w/v %, preferably 0.5–2 w/v %. Gelation is carried out under an atmosphere of gas such as ammonia gas for about several minutes to about 2 hours as occasion demands. Then lyophilization is carried out.

The main wave length of ultraviolet rays used for crosslinking is preferably 250–270 nm. Ultraviolet rays may be irradiated in a dose of 500–12000 mWsec/cm$^2$, preferably 1000–5000 mWsec/cm$^2$. Examples of the crosslinking agent used in the present invention are, for instance, glutaraldehyde, ethylene glycol diglycidyl ether, polyglycerol polyglycidyl ether, glycerol polyglycidyl ether, hexamethylene diisocyanate and the like. Also, the size of the collagen sponge is suitably selected depending on size of the wound to be covered. Although the thickness and shape of the collagen sponge change depending on conditions of the wound to be covered, thickness the may be 0.2–30 mm, and the sponge may be formed in a sheet-like shape, a laminar shape, a cylinder shape, a globular shape, a spindle shape or a lenticular shape.

The collagen sheet used in the present invention can be prepared by pouring a collagen solution into the vessel as used in the above-mentioned preparation of the collagen sponge, air-drying the solution in a dryer to give a sheet, and then introducing intermolecular-crosslinking into the sheet with irradiation of ultraviolet rays or a crosslinking agent.

The collagen solution used in the preparation of the above-mentioned collagen sheet is obtained by preparing collagen from a bovine dermis or the like, adjusting pH of a solution of the collagen to preferably 2–4 and preparing the collagen solution in a concentration of 0.2–3 w/v %, preferably 0.5–2 w/v %.

The main wave length of ultraviolet rays used for crosslinking is preferably 250–270 nm. Ultraviolet rays may be irradiated in a dose of 500–12000 mW sec/cm$^2$, preferably 1000–5000 mWsec/cm$^2$. Examples of the crosslinking agent used in the present invention are, for instance, glutaraldehyde, ethylene glycol diglycidyl ether, polyglycerol polyglycidyl ether, glycerol polyglycidyl ether, hexamethylene diisocyanate and the like. Also, the size and thickness of the collagen sheet suitably selected depending on conditions of the wound to be covered.

The collagen gel used in the present invention can be prepared by pouring a collagen solution into the vessel as used in the above-mentioned preparation of the collagen sponge, and heating the solution or allowing the solution to stand under an atmosphere of ammonia gas to give a gel.

The collagen solution used in the preparation of the above-mentioned collagen gel is obtained by preparing collagen from a bovine dermis or the like, adjusting pH of a solution of the collagen to preferably 2–4 and preparing the collagen solution in a concentration of 0.2–3 w/v %, preferably 0.5–2 w/v %. Gelation is carried out under an atmosphere of an alkaline gas such as ammonia gas for about several minutes to about 2 hours as occasion demands. After gelation, the gel is sufficiently rinsed with a buffer or the like. In case of gelling a neutral solution of collagen (pH 6.5–8), the solution in a concentration of a 0.1–1 w/v %, preferably 0.2–0.5 w/v % is allowed to stand at 36°–40° C. without using any alkaline gas or the like to give a gel.

Main wave length of ultraviolet rays used for crosslinking is preferably 250–270 nm. Ultraviolet rays may be irradiated in a dose of 500–12000 mWsec/cm$^2$, preferably 1000–5000 mWsec/cm$^2$. Examples of the crosslinking agent used in the present invention are, for instance, glutaraldehyde, ethylene glycol diglycidyl ether, polyglycerol polyglycidyl ether, glycerol polyglycidyl ether, hexamethylene diisocyanate and the like.

Also, the size of the collagen gel is suitably selected depending on size of the wound to be covered. Although the thickness and shape of the collagen gel change depending on conditions of the wound to be covered, the thickness may be 0.2–30 mm, and the gel may be formed in a sheet-like shape, a laminar shape, a cylinder shape, a spindle shape or a lenticular shape.

The culture skin of the present invention is prepared so as to produce a penetrating pore by locating a projection in the culture skin in order to smoothly carry out the nutrition supply from a covered wound face to cells seeded on the culture skin and the discharge of exudate excessively pooled in the covered part with inhibiting the contraction of the culture skin. The means for producing the above-mentioned penetrating pore does not need a particular pretreatment and the like on purpose to prevent from flowing out and being lost in the process of cells seeding them, such as gel coating.

Examples of such means for producing a penetrating pore with inhibiting contraction of the culture skin are, for instance, a support having a projection, a vessel having a projection, and a support or vessel having a projection with a removable sheet and the like, which are used in preparing the culture skin matrix and removed before the covering with the culture skin.

The support has preferably a skeleton of a network, and a projection is located on the skeleton.

The shape of a mesh of a network forming the skeleton in the above-mentioned support is not particularly limited, however, a preferable shape is, for instance, a polygon, a circle, an oval or the like. It is not necessarily required that meshes are in the same shape throughout the network. Although the size of an open space may suitably change, preferably open spaces occupy at least half of the area of the support and are positioned uniformly on the support. The distance between intersecting points in a network may be from 5 to 30 mm, preferably 7 to 20 mm. The thickness of the support is preferably thin to the extent that the support is not broken.

The shape, number and size of the projection are not particularly limited. However, it is preferable that the preparation and handling of the projection are easy. It is enough that the height of the projection is at least the thickness of the obtained matrix The preferable projection has suitable size or shape to occupy an area of 0.003 to 0.25 cm$^2$/cm$^2$, more preferably 0.01 to 0.12 cm$^2$/cm$^2$ to produce an open space. Examples of the shape to be suitably used are, for instance, a columnar shape, a conical shape, a shape of a polygonal prism, a shape of a polygonal pyramid and the like. The top of these shapes may be globular.

In the case of seeding, culturing and proliferating cells on one side (and inside) of the culture skin matrix, the skeleton of the support may be a plate without an opening such as a mesh. Such support is the above-mentioned plate wherein a projection is located on at least one side thereof.

As another way, projection may be directly located in the bottom of the vessel to prepare the culture skin in the present invention, which is in the same form as the same mentioned above.

The above-mentioned support, vessel and these projections are made of e.g., plastics, stainless steel, aluminium, glass, ceramics or the like. The material of the support is preferably flexible so the culture skin is easily removed from the support in case of covering a wound face with the culture skin.

It is preferable to design a skeleton of the above-mentioned support and vessel so as to give a structure in which penetrating pores are uniformly produced, and projections are uniformly located. That is because, contraction of the culture skin can be well inhibited, and nutrition can be pervided throughout the culture skin, and discharge of exudate from the covered wound can be efficiently carried out.

Figure 1:
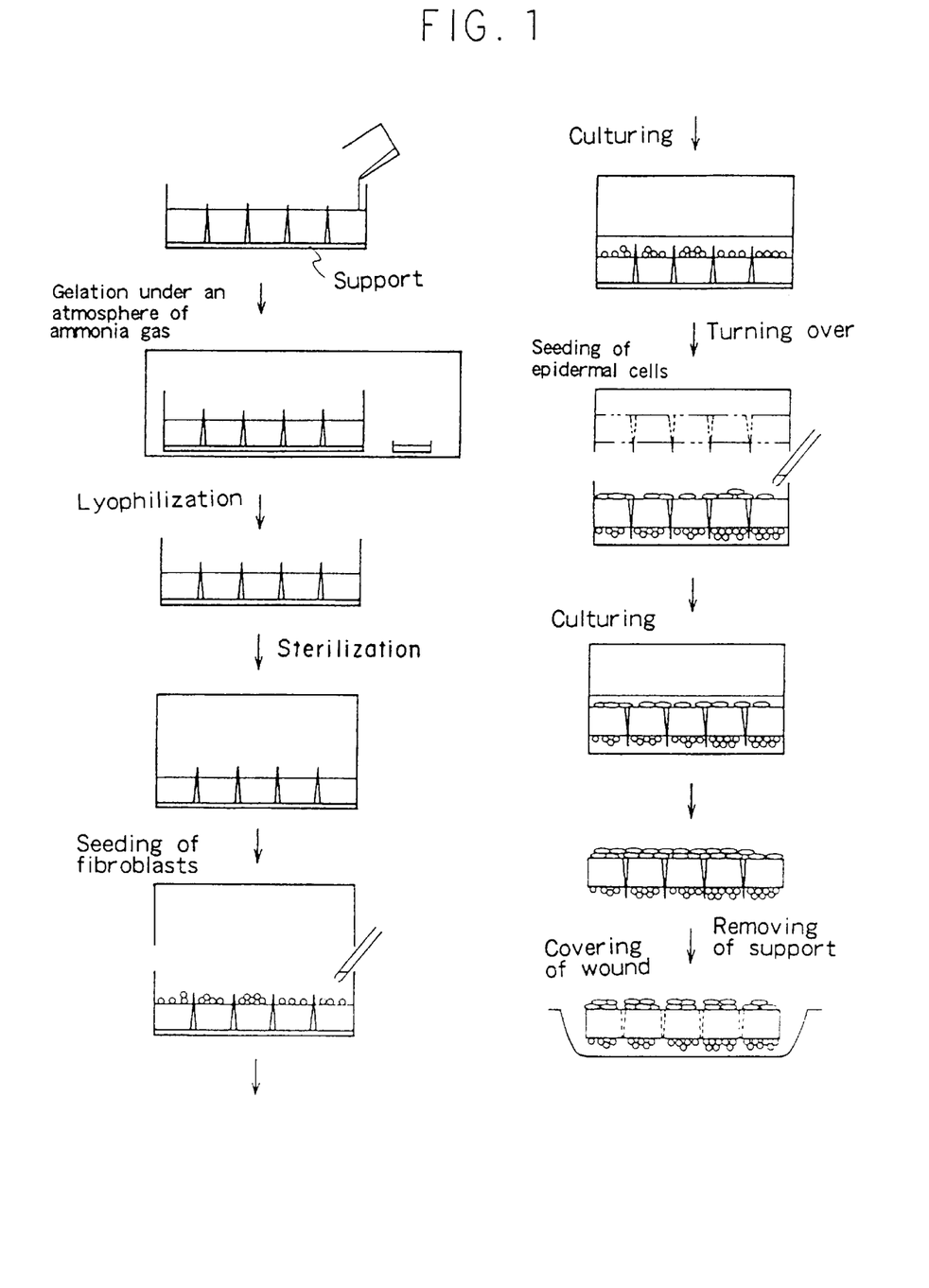
FIG. 1 is a scheme showing procedures for preparing a composite culture skin which is provided with penetrating pores using the support according to the present invention.
Figures 2A, 2B:
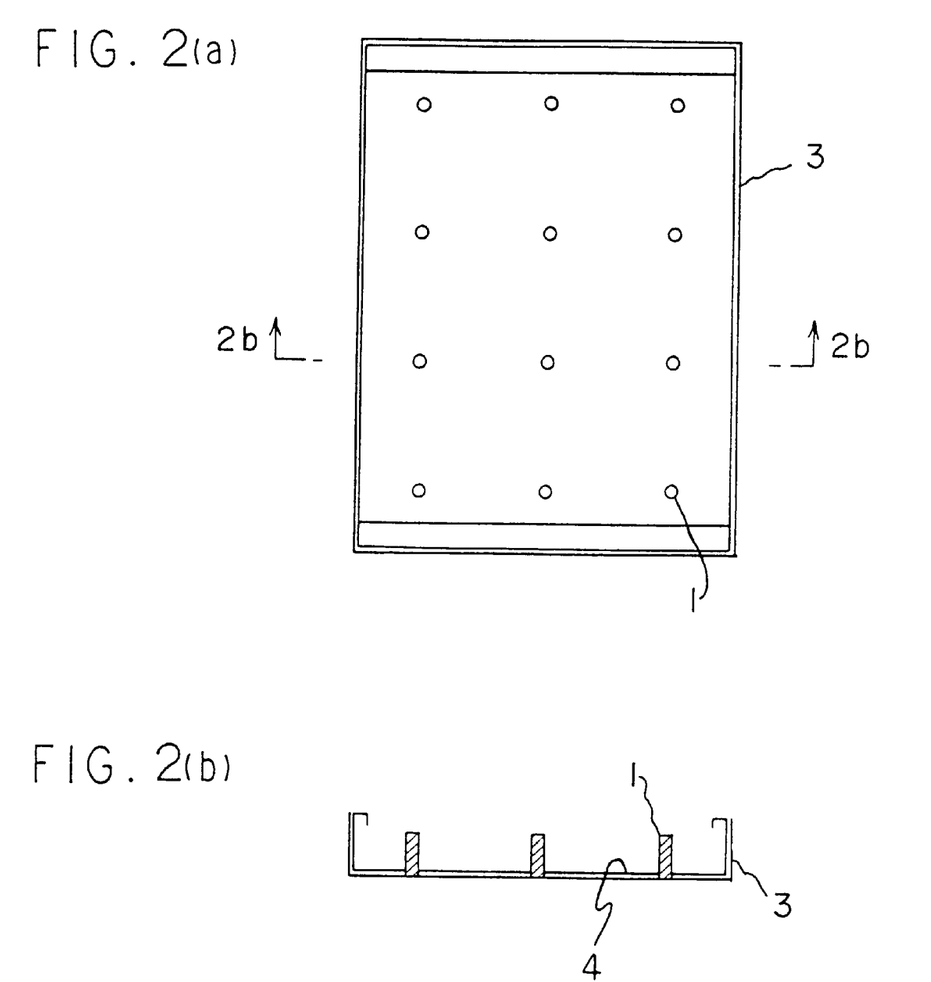
FIG. 2(a) is a top view of a vessel having projections and a removable sheet according to the present invention.
FIG. 2(b) is a view taken on line A–B.
Figure 3A:
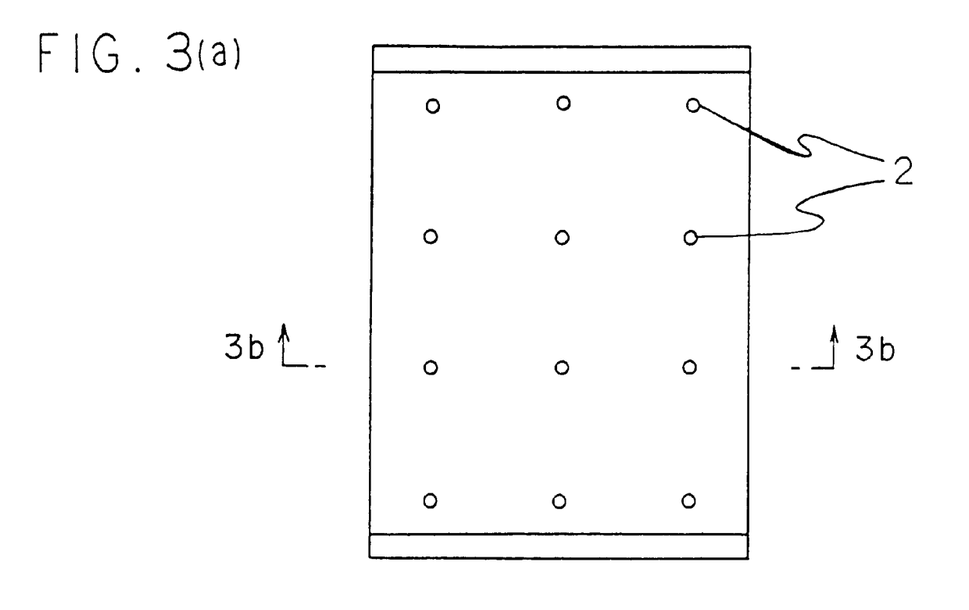
FIG. 3(a) is a top view of a removable sheet which is located in the above-mentioned vessel.
Figure 3B:
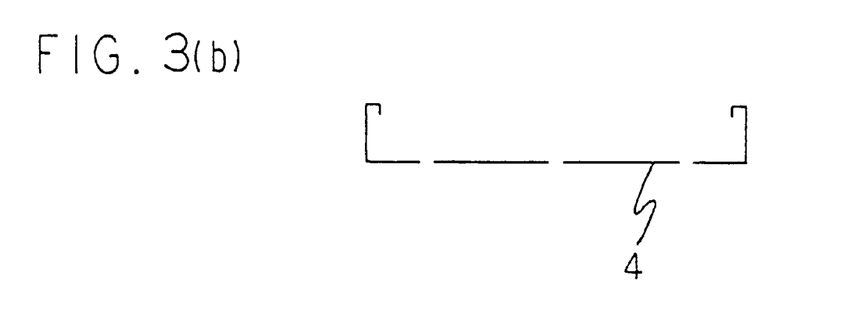
FIG. 3(b) is a view taken on line C–D.
Figure 4:
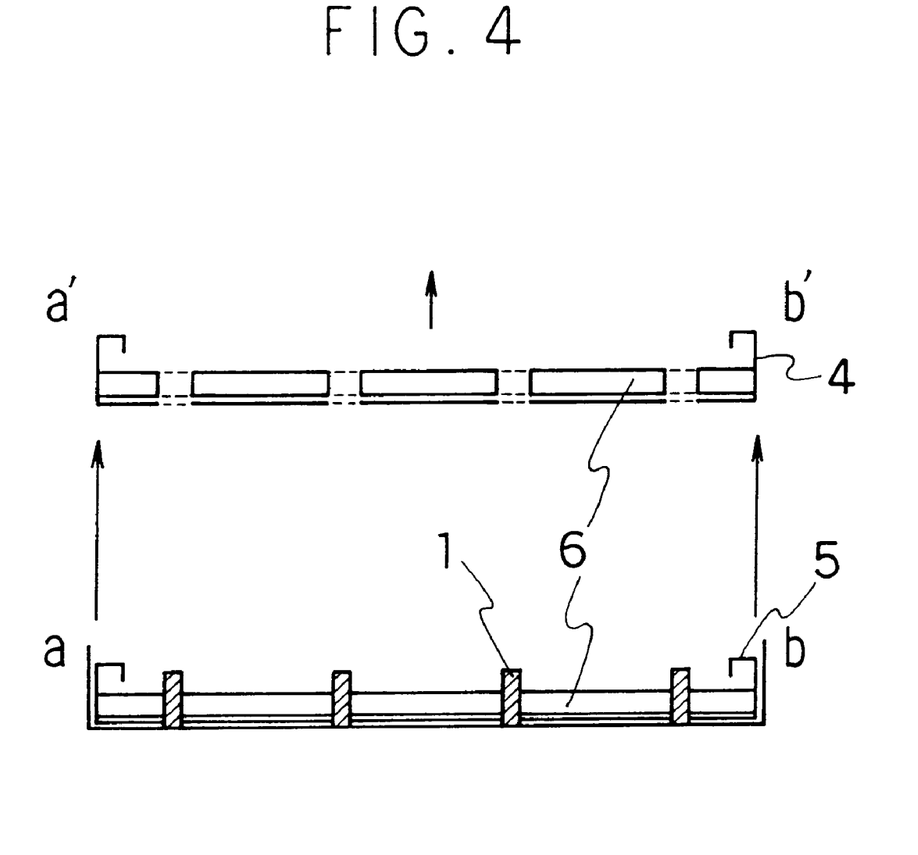
FIG. 4 is a sectional view of the culture skin prepared in the above-mentioned vessel taken on line a–b (lower) and a sectional view of a removable sheet with the culture skin which is taken from the above-mentioned vessel taken on line a'–b' (upper).

Further, as the above-mentioned support or vessel having a projection may be used one with a removable sheet. The removable sheet is preferably made of flexible material so as to permit turning up of the ends of the sheet to easily remove the culture skin from the support or vessel in the case of covering a wound face with the culture skin (see 5 in FIG. 4). Examples of the sheet are, for instance, a plastic sheet, a stainless steel sheet, an aluminous sheet and the like.

However, it is understood that in the processes of the present invention there can be used the means by which a penetrating pore can be produced to smoothly carry out the nutrition supply to cells seeded on the culture skin matrix of the present invention and the discharge of exudate excessively pooled in the covered wound, and simultaneously contraction of the culture skin is inhibited, provided that the means does not need any particular pretreatment and the like in order to prevent the flow and loss of cells during the seeding of cells.

On at least one side of the culture skin matrix of the present invention, mammalian skin-derived epidermal cells and/or fibroblasts are seeded, cultured and propagated. The term "epidermal cells" described above means cornificated cells including basal cells and other cells normally existing in an epidermal cell's layer. Among them, cells to be cultured and propagated are cornificated cells. The term "fibroblasts" described above means main cells in the dermis, which produce connective tissue ingredients such as collagen and the like and form a connective tissue by binding with these ingredients.

As the culture skin of the present invention, the following three kinds of skins can be prepared according to cells to be seeded:

(1) the culture skin wherein only fibroblasts are seeded and cultured preferably on (and in) both sides, at least one side of the collagen matrix of the present invention (composite culture dermis), (2) the culture skin wherein epidermal cells are seeded and cultured on one side of the collagen matrix of the present invention (composite culture epidermis) and (3) the culture skin wherein fibroblasts are seeded and cultured on (and in) at least one side of the collagen matrix of the present invention, and epidermal cells are seeded and cultured on one side of the above-mentioned matrix (composite culture skin).

In the case of the culture skin (3), it is more preferable to previously carry out the step in which fibroblasts are seeded and cultured, because epidermal cells can be prevented from falling. However, the step in which fibroblasts are seeded and cultured can be carried out after the epidermal cells are previously seeded, cultured and propagated.

The above-mentioned three kinds of culture skins show better effects by properly using them according to area and depth of the wound and conditions of a patient to be treated and the like. Also, these culture skins can be properly used as autologous skins or as alogenic skins.

The above-mentioned epidermal cells are prepared according to the following procedure. A skin (epidermis and split-thickness or full-thickness of dermis) taken under a clean environment is disinfected and immersed in physiological saline or a buffer such as Hank's solution which contains an antibiotic. The skin is immersed in the Dulbecco's modified Eagle's minimum essential medium (DMEM) containing dispase in a concentration of 1000 U/mL (hereinafter referred to as "dispase solution"), and then separated into epidermis and dermis. After immersing the obtained epidermis in Hank's solution containing trypsin in a concentration of 0.25 w/v % and ethylenediaminetetraacetic acid trisodium salt (EDTA) in a concentration of 0.005 mM/mL (hereinafter referred to as "trypsin solution") at 37° C. for about 15 minutes, the epidermis is transferred to a medium such as DMEM containing 10 v/v % fetal calf serum (FCS) (hereinafter referred to as "DMEM+10% FCS") and shaken to disperse the cells. The cells are collected by centrifuging at about 400×g for 5 minutes to give epidermal cells. Thus obtained epidermal cells are added to, for instance, Green medium, NCTC 168 medium or MCDB 153 medium, most preferably Green medium to give a suspension of epidermal cells. The above-mentioned Green medium is an epidermal cell growth medium obtained by mixing DMEM and Ham's F-12 in a mixing ratio of DMEM : Ham's F-12 being 3 : 1 and adding hydrocortisone (0.4 $\mu$g/mL), insulin (5 $\mu$g/mL), transferrin (5 $\mu$g/mL), triiodothyronine (0.0013 $\mu$g/mL), choleratoxin (0.01 $\mu$g/mL), adenine (24.3 $\mu$g/mL), epidermal growth factor (0.01 $\mu$g/mL) and an antibiotic thereto, which comprises 10% FCS (see Cell, 40, pages 677–683, March, 1985).

In order to propagate the above-mentioned epidermal cells with high efficiency, it is preferable to culture the cells in a culture flask in which 3T3 cells mouse-derived fibroblasts are fixed as feeder cells, the propagation ability of which is stopped by mitomycin treatment or irradiation of radiation, or the like.

Specifically, the 3T3 cells are cultured, and then the medium is removed. The cells are rinsed with Hank's solution, and the solution is removed. Successively to the cells is added a DMEM solution containing mitomycin C in a concentration of (4 $\mu$g/mL) so as to fully immerse the cells as a whole in the solution (about 2–about 4 mL is preferable in a 75 cm$^2$ culture flask), and the cells are allowed to stand at 37° C. for about 2 hours. Then the cells are washed with a buffer to remove mytomycin C. Thus only the propagating ability of the 3T3 cells is stopped, although the cells are alive. The 3T3 cells having no proliferating ability are collected and suspended in the above-mentioned Green medium. After preparing a cell suspension with a cell density of $1 \times 10^3$–$5 \times 10^4$ cells/cm$^2$, preferably $5 \times 10^3$–$3 \times 10^4$ cells/cm$^2$, the cell suspension is seeded in a culture flask. After seeding the 3T3 cells, the above-mentioned epidermal cells are seeded in the flask with a cell density of $5 \times 10^3$–$5 \times 10^5$ cells/cm$^2$, preferably $1 \times 10^4$–$2 \times 10^5$ cells/cm$^2$.

The above-mentioned epidermal cells obtained from a split-thickness skin (e.g., about 2×2 cm) are cultured at 37° C. under 5% $CO_2$ in an incubator. The 3T3 cells hardly mingle with epidermal cells which are finally obtained, because the 3T3 cells come from the bottom of the flask to the medium in the stage wherein epidermal cells form a colony for the duration of culturing the epidermal cells to remove the 3T3 cells in changing the medium.

The cultured and proliferated epidermal cells are removed by adding the dispase solution thereto and allowing it to stand at 37° C. for about 2 hours. The obtained epidermal cells are dispersed by adding the trypsin solution thereto, and then collected. A cell suspension is obtained by adding the Green medium to the collected cells. The epidermal cells are sub-cultured as occasion demands. Concretely, the above-mentioned feeder cells are prepared in a necessary quantity, and the epidermal cells which are cultured and propagated as described above are collected, then the epidermal cells are seeded and cultured on the feeder cells. At this point, passage culture is carefully carried out so that cornification of the epidermal cells is not caused. The obtained epidermal cells are seeded on the collagen spongy matrix (e.g., about 6×9.5 cm, thickness: 1 mm) with a cell density of e.g., $5 \times 10^4$–$2 \times 10^5$ cells/cm$^2$.

After the epidermal cells adhere to the matrix, thereto is added the Green medium. Then, the cells are cultured under 5% $CO_2$ in an incubator at 37° C. for 7–21 days with changing of the medium every 3 days. Thus the composite culture epidermis can be obtained.

The above-mentioned fibroblasts are collected by separating a removed skin into epidermis and dermis, sucessively breaking the obtained dermis with scissors, a homogenizer or the like, adding the broken dermis to DMEM solution containing 0.5 w/v % collagenase (hereinafter referred to as "collagenase solution"), shaking the mixture for about 6 hours at about 37° C. to dissolve a connective tissue, and centrifuging the mixture at about 400×g–about 1,000×g, preferably about 600×g–about 800×g. The thus obtained fibroblasts are cultured in a culture flask with a medium such as DMEM+10% FCS under 5% $CO_2$ in an incubator at 37° C. to give a sub-confluent culture. As occasion demands, passage culture is carried out so that a number of fibroblasts are obtained.

The cultured fibroblasts are removed from the flask with the trypsin solution, collected and prepared into a cell suspension in DMEM+10% FCS. The fibroblast suspension is seeded with a cell density of $5 \times 10^3 - 5 \times 10^5$ cells/cm$^2$, preferably $5 \times 10^4 - 2 \times 10^5$ cells/cm$^2$ on the collagen matrix. After the fibroblasts adhere to the matrix, thereto is added DMEM+10% FCS. Then, the fibroblasts are cultured under 5% $CO_2$ in an incubator at 37° C. for 1–14 days with changing the medium every 3 days. Thus the composite culture dermis can be obtained. The composite culture dermis is obtained by culturing and propagating fibroblasts on (and in) at least one side of the matrix.

The composite culture skin having both of epidermal cells and dermal cells (fibroblasts) is prepared as described below. According to the step of preparing the above-mentioned composite culture dermis, fibroblasts are seeded. After the cells are well adhered to the matrix, the matrix is turned over together with the support. Then, the step of preparing the composite culture epidermis is carried out to give the composite culture skin.

Preferably, the thus obtained culture skin is washed with DMEM and replaced in the similar medium containing no FCS before covering a wound with the culture skin.

In the culture skin using the matrix of the present invention, discharge of exudate in the wound is favorably performed by producing a penetrating pore before the covering of a wound therewith as described above, while in a culture skin using a matrix wherein no penetrating pore is produced, exudate and the like are excessively pooled in the wound to give a hotbed of infection. Therefore, the culture skin of the present invention is extremely useful for forming a good granulation tissue.

Hyaluronic acid used in the culture skin of the present invention is a biologically active substance which is produced from a cell at the first stage when a wound and the like are caused. It is stated that in the healing course of a wound, hyaluronic acid is necessary to both of epidermal cells and fibroblasts in order to favorably move on a collagen matrix. It is considered that hyaluronic acid fulfils a function of facilitating the moving of cells by making anchoring of cells easy. In preparing the collagen matrix, hyaluronic acid is used in a concentration of 0.1–5% of that of collagen to be used.

A more preferable culture skin of the present invention is obtained by coating fibronectin, laminin or the like as a cell adhesion factor on the matrix of the present invention in order to improve adhesion on the matrix.

The present invention is more specifically described and explained by means of the following Examples and Comparative Example. It is to be understood that the present invention is not limited to the Examples, and various changes and modifications may be made in the invention without departing from the spirit and scope thereof.

EXAMPLE 1

Preparation of the atelocollagen gel wherein penetrating pores were produced with the support having projections according to the present invention.

In a plastic case (6×9.5 cm, height: 2.8 cm) was placed a plastic support (5.5×9 cm) having networks of which opening was 7×7 mm and on which projections being regular square prisms (length: 7 mm, 1×1 mm) were located at intervals of 8 mm of longitudinal length and 8 mm of lateral length. Into the plastic case was poured 20 mL of DMEM solution containing 0.2 w/v % atelocollagen (pH 7.4, made by KOKEN CO., LTD.). The case was allowed to stand at 37° C. for 1 hour for gelation, and irradiated with UV of 2 mW/cm$^2$ for 30 minutes to give an atelocollagen gel having a thickness of 0.3 cm.

EXAMPLE 2

Preparation of the composite culture dermis (in a form of gel) wherein penetrating pores were produced with the support having projections according to the present invention.

A piece of human skin (about 2 cm×about 2 cm, thickness: about 0.5 mm) which was taken under a clean environment was immersed in ISODINE® solution (made by Meiji Seika Co., Ltd.), and washed with Hank's solution. Then the piece was immersed in Hank's solution containing streptomycin (1000 μg/mL), penicillin (1000 U/mL), amphotericin B (2.5 μg/mL) at room temperature for 30 minutes.

Successively the piece was immersed in 10 mL of the dispase solution (dispase was made by GODOSHUSEI CO., LTD.) at 4° C. for 12 hours. The piece was separated into epidermis and dermis by a pincette. The obtained dermal part was broken with scissors to give paste. The paste was treated with 10 mL of the collagenase solution (collagenase was made by Wako Pure Chemical Industries, Ltd.) for about 6 hours at 37° C. to remove a connective tissue. Then fibroblasts were obtained by centrifuging it at about 700×g for 5 minutes. The thus obtained fibroblasts were sub-cultured with DMEM (made by GIBCO)+10% FCS under 5% $CO_2$ in an incubator at 37° C. in a plastic culture flask with changing of the medium every 3 days to propagate fibroblasts.

Thereafter the fibroblasts were removed with a trypsin solution (trypsin was made by DIFCO) from the flask. The fibroblasts were seeded with a cell density of $5 \times 10^4$ cells/cm$^2$ on the atelocollagen gel prepared in Example 1. After seeding, the fibroblasts were allowed to stand as they were at room temperature for 12 hours so that fibroblasts adhered to the gel. Successively thereto was added 15 mL of the above-mentioned DMEM+10% FCS. The fibroblasts were cultured under 5% $CO_2$ in an incubator at 37° C. for 7 days with changing the medium every 3 days to give a composite culture dermis which had been equipped with the support.

The composite culture dermis of the present invention was prepared by the means which does not require any pretreatment in order to prevent cells from flowing out and being lost in seeding cells on a culture skin matrix, of which the contraction ratio was remarkably lowered. Further the above-mentioned culture dermis could be applied to a wound together with the support in case of covering the wound, and thereafter penetrating pores were produced by removing the support. Use of the composite culture dermis of the present invention enabled favorable supply of nutrition to cells and to discharge of exudate from an implanted part of the wound.

EXAMPLE 3

Preparation of the atelocollagen sponge wherein penetrating pores were produced with the support having projections according to the present invention With a homogenizer (made by NIHONSEIKI SEISAKUSHO CO., LTD.), 100 mL of an aqueous solution of atelocollagen (made by KOKEN CO., LTD.) prepared in a concentration of 1 w/v % the pH, of which was adjusted to 4 with hydrochloric acid, was stirred for 1 minute to put bubbles into the solution. In a plastic case (6×9.5 cm, height: 2.3 cm) was placed a plastic support (5.5×9 cm) having networks of which the opening was 7×7 mm and on which projections in a columnar shape (length: 8 mm, diameter: 1 mm) were located at intervals of 8 mm of longitudinal length and 8 mm of lateral length. Into a bottom of the plastic case was poured 25 mL of the solution. After the case was allowed to stand for 1 hour under an atmosphere of ammonia gas, lyophilization was carried out to give an atelocollagen sponge having a thickness of about 1 mm. Then the obtained sponge was irradiated with UV of 1 mW/cm$^2$ for 30 minutes on one side thereof. Sucessively the sponge was sterilized with ethylene oxide gas which was placed in the plastic case as it was.

EXAMPLE 4

Preparation of the composite culture skin (in a form of sponge) wherein penetrating pores were produced with the support having projections according to the present invention.

Epidermis was separated from human skin (about 2 cm×about 2 cm, thickness: about 0.5 mm) which was taken under a clean environment in the same manner as described in Example 2. The epidermis was put into 10 mL of the trypsin solution to treat it therein for 15 minutes at 37° C. Then the treated epidermis was put into DMEM+10% FCS which was the same as that used in Example 2. The epidermal cells were shaken to disperse them, and collected by precipitating with centrifugation at about 400×g for 5 minutes. The obtained epidermal cells were suspended in the Green medium the composition of which was described above. In order to propagate epidermal cells with high efficiency, the following feeder cells were used. 3T3 cells which are mouse-derived fibroblasts were cultured in a culture flask with the above-mentioned DMEM+10% FCS under 5% $CO_2$ in an incubator at 37° C. to give a subconfluent culture. Then the culture was rinsed with Hank's solution after removing the medium. To the culture was added DMEM being which is the same as that used in Example 2. Further thereto was added a physiological saline containing mitomycin C (made by WAKO PURE CHEMICAL INDUSTRIES, LTD.) (0.1 mg/mL) to give a final concentration of 0.0004% as to mitomycin C. The flask was allowed to stand at 37° C. for 2 hours. Then the flask was washed with Hank's solution to remove mitomycin C. 3T3 cells the propagating ability of which was stopped were collected. The obtained cells were suspended in the Green medium and seeded in a culture flask with a cell density of 2×10$^4$ cells/cm$^2$ after cell counting.

On the day following the seeding of the thus prepared 3T3 cells, the above-mentioned epidermal cells were seeded thereto, cultured and propagated at 37° C. under 5% $CO_2$ in an incubator.

On the other hand, fibroblasts were seeded with a cell density of 1×10$^4$ cells/cm$^2$ as described in Example 2 on the atelocollagen sponge obtained in Example 3, and cultured with the above-mentioned DMEM+10% FCS for 2 days. Then the medium was removed, and the atelocollagen sponge was turned over together with the support in the case. The epidermal cells which were cultured and propagated as described above, were seeded with a cell density of 2×10$^5$ cells/cm$^2$ from the back side of the support to the back side of the sponge. The case containing the sponge was allowed to stand for 8 hours in a clean bench. Then thereto was added the Green medium, and the cells were cultured under 5% $CO_2$ in an incubator at 37° C. for 14 days with changing the medium every 3 days to give a composite culture skin.

EXAMPLE 5

Preparation of the culture skin matrix (in a form of sponge) containing hyaluronic acid After 1 g of atelocollagen (made by KOKEN CO., LTD.) was dissolved in distilled water the pH of which was adjusted to 3 with hydrochloric acid, thereto was added an aqueous solution of sodium hydroxide to give an aqueous solution of atelocollagen the pH of which was adjusted to 4.5. Then 0.01 g of hyaluronic acid (molecular weight: about 2×10$^6$) was dissolved in the aqueous solution of atelocollagen, and thereto was added distilled water the pH of which was adjusted to 4.5 to give a total amount of 100 mL (the solution containing 1 w/v % atelocollagen and 0.01 w/v % hyaluronic acid). The solution was homogenized for 1 minute, and then 25 mL of the aqueous solution containing atelocollagen and hyaluronic acid was poured onto the bottom of a case (6×9.5 cm, height: 2.3 cm) wherein the support having projections was placed. In the support having projections, the projections were regular square prisms (length from the support: 8 mm, 2×2 mm) and located at an interval of 7 mm from each other. The case was allowed to stand for 2 hours under an atmosphere of ammonia gas to give a gel. The gel was washed with water and lyophilized.

The lyophilized gel was irradiated with UV of 1 mW/cm$^2$ for 30 minutes, and then sterilized with ethylene oxide gas to give an atelocollagen matrix contaning hyaluronic acid.

In the same manner as described in Example 2, fibroblasts were seeded, cultured and propagated on and in the thus obtained matrix. The matrix was removed from the support to give a composite culture dermis having penetrating pores the contraction ration of which was low.

In the back of a nude mouse a full-thickness skin defect (2×2 cm) was prepared. The composite culture dermis was cut so as to match the defect in size and implanted on the defect. Two weeks after covering the defect with the composite culture dermis, it was observed that no exudate was pooled in the covered part and that a granulation tissue was favorably formed. Favorable healing course was shown.

EXAMPLE 6

Preparation of the composite culture dermis wherein penetrating pores were produced with the vessel having projections with a removable sheet A vessel (6×9.5 cm) was prepared wherein projections of square prisms (regular square prisms: height 7 mm, 2×2 mm) were located at the bottom. On the bottom of the vessel, a sheet made of polyester wherein parts corresponding to position where projections were located were cut out, was placed. The sheet was provided with grips.

Fibroblasts and 20 mL of 0.2% DMEM neutral solution of collagen (CELLGEN®, made by KOKEN CO., LTD.) were mixed, and the cell mixture was prepared so as to give a cell density of 1×10$^5$ cells/cm$^2$.

The mixture was poured into the above-mentioned vessel. The vessel was covered with the lid and allowed to stand at 37° C. for 5 hours. Then thereto was added DMEM+10% FCS in the same manner as in Example 2, and the cells were cultured for 1 week to give a composite culture dermis. In the case of covering a wound, the lid was taken off, and the composite culture dermis and the sheet were easily taken off from the vessel by lifting the grips of the sheet. Thereby penetrating pores were produced, and the composite culture dermis could be easily taken off from the sheet.

Comparative Example 1

The procedure in Example 6 was repeated except that there was used a vessel wherein no projection was located. Five days after the beginning of seeding and culturing of cells, the collagen gel was extremely contracted. The collagen gel had an area of about 25% and a volume of about 15% of those of the composite culture dermis obtained in Example 6, respectively.

In addition to the ingredients used in the Examples, other ingredients can be used in the Examples as set forth in the specification to obtain substantially the same results.

What is claimed is:

1. A process for preparing a skin cell culture comprising the steps of:

a) preparing a skin cell culture matrix comprising a collagen sponge, a collagen sheet or a collagen gel in a means having a plurality of projections to provide said matrix with penetrating pores, b) seeding and culturing skin-derived cells on said matrix, and c) producing a plurality of penetrating pores on said matrix bearing the skin cell culture before the covering of a wound, wherein steps a) and b) are carried out sequentially or simultaneously.

2. The process of claim 1, wherein step b) is:
   (i) a step in which skin-derived fibroblasts are seeded and cultured on one side or both sides of said matrix, or
   (ii) a step in which epidermal cells are seeded and cultured on one side of said matrix, or
   (iii) a step in which skin-derived fibroblasts are seeded and cultured on one side or both sides of said matrix and epidermal cells are seeded and cultured on one side of said matrix.

3. The process of claim 1 or 2, wherein said means provided with a plurality of projections is a support plate provided with said projections, or a vessel with a bottom of which the inner surface is provided with said projections.

4. The process of claim 3, wherein said support plate or said bottom of said vessel is fitted with a removable sheet having perforations matching said projections, and said skin cell culture is provided on said removable sheet.

5. The process of claim 1 or 2, wherein the collagen is atelocollagen.

6. The process of claim 1 or 2, wherein the skin cell culture matrix contains hyaluronic acid.

* * * * *